United States Patent

Kirchhuebel et al.

Patent Number: 5,870,168
Date of Patent: Feb. 9, 1999

[54] VISION-TESTING DEVICE

[75] Inventors: Rainer Kirchhuebel, Asslar; Carsten Feiertag, Hungen, both of Germany

[73] Assignee: Oculus Optikgeraete GmbH, Wetzlar, Germany

[21] Appl. No.: 934,441

[22] Filed: Sep. 19, 1997

[30] Foreign Application Priority Data

Sep. 20, 1996 [DE] Germany .................. 296 16 443.7

[51] Int. Cl.$^6$ ........................................................ A61B 5/14
[52] U.S. Cl. .............................................. 351/221; 351/211
[58] Field of Search ..................................... 351/221, 211, 351/205, 200, 246, 213, 214, 216, 217, 218

[56] References Cited

U.S. PATENT DOCUMENTS 5,793,469  8/1998  Feiertag et al. ........................ 351/221

FOREIGN PATENT DOCUMENTS 23 21 570  11/1974  Germany .
24 09 747   9/1975  Germany .
30 03 588   8/1981  Germany .

*Primary Examiner*—Hung Xuan Dang
*Attorney, Agent, or Firm*—Flynn, Thiel, Boutell & Tanis, P.C.

[57] ABSTRACT

A vision-testing device for examining the crepuscular vision, which has several visual signs which can be placed at random into the beam path, and a glare light source, all in a closed housing. The device has in extension of the axis of the eye a partially transparent mirror inclined with respect to the axis of the eye and a refractive element. The vision-testing device is compact, light and robust in design and enables a testing of the crepuscular visual acuity and the dazzle sensitivity. The refractive element consists of an achromatic lens inserted into the beam path, and covering the visual range of both eyes or a concentrating reflector, at the focal point of which is provided the visual sign location. The carrier for the visual signs to be located at the visual sign location can be arranged movably such that any of the multiple visual signs placed on the carrier can be moved into the beam path. A filter can also be swung into and out of the beam path between the light source and the visual sign location. The glare light source is arranged stationarily next to the transilluminated visual sign location. One or several diaphragms with varying diaphragm openings are provided above the visual sign carrier, which diaphragms can be moved selectively into the beam path.

17 Claims, 3 Drawing Sheets

VISION-TESTING DEVICE

FIELD OF THE INVENTION

The invention relates to a vision-testing device, in particular for examining the crepuscular vision, with several visual signs which are to be randomly placed into the beam path, with a glare light source which can be selectively blocked and unblocked and is arranged next to a visual sign location, all within a closed housing having a viewing opening for the testing person and an opening lying in an extension of the axis of the eye, which opening indeed enables an unhindered looking out, however, is provided with a filter for reducing the incoming outside light, wherein in extension of the axis of the eye there is arranged a partially transparent mirror inclined with respect to said axis, and a refractive element arranged in the beam path extending from the eye to the visual sign location.

BACKGROUND OF THE INVENTION

A vision-testing device of the above-identified type, which is used to examine the crepuscular visual acuity and glare sensitivity, is known from the DE-C-30 03 588. A screen is used in this vision-testing device for examining the crepuscular vision and the dazzle sensitivity, which screen is illuminated by two projectors simultaneously, whereby in the beam path of the one projector there is arranged a visual optotype and the light intensities of both projectors are coupled with one another such that the light intensity of the one projector increases in the same manner as the one of the other projector decreases. This known vision-testing device, which is a clear-vision device, is expensive to make, demands four projectors and many adjustable mirrors in order to create the desired visual sign. This relatively complicated device requires also a large housing and a relatively heavy construction thereby making its transporting ability is limited.

Furthermore vision-testing devices are known from the DE-A 24 09 747 and the DE-A 2 321 570 and have a closed housing, however, do not guarantee clear vision. Moreover these devices demand that a pair of lenses be arranged in front of each eye, which pair of lenses must be very precisely focused so that the visual sign is viewed as a unit and a jump or a shift in the visual sign does not occur. Such devices are, on the one hand, complicated to adjust and are moreover also sensitive to impact so that their transporting ability is limited. It is known from these references to arrange the visual signs on a disk-shaped carrier, which is transilluminated by a light source.

The basic purpose of the invention is to provide a vision-testing device of the above-identified type in such a manner that same is, on the one hand, compact and light and furthermore robust in design, which permits a testing of the crepuscular visual acuity and the dazzle sensitivity, and in addition as a variation to determine the daytime visual acuity or stepped vision values under crepuscular conditions. A further purpose of the invention is to provide a vision-testing device in such a manner that it can be computer-controlled operated and thus the testing input can be significantly reduced.

SUMMARY OF THE INVENTION

This purpose is attained according to the invention in such a manner that the refractive element is an achromatic lens inserted into the beam path, covering the visual range of both eyes, or is a concentrating reflector, at the focal point of which is provided the visual sign (or optotype), that the visual sign or visual signs are applied onto a carrier and are transilluminated by a light source, that the carrier for the visual signs is arranged swingably or movably such that any visual signs applied onto the carrier can be moved into the beam path, that a filter can be swung into and out of the beam path between the light source and the visual sign, that the glare light source is arranged stationarily next to the transilluminated visual sign location, and that above the visual sign carrier there are provided one or more diaphragms with varying diaphragm openings which can be moved selectively into and out of the beam path.

The visual signs (or optotypes) are according to the invention applied, advantageously coated, onto a test carrier, whereby these visual signs are transilluminated by one single light source, wherein an illumination beam path is provided in which advantageously one single achromatic lens is arranged. Furthermore a partially transparent mirror is arranged in the beam path, which mirror lies in an extension of the axis of the eye so that a clear vision device is obtained through an opening lying on the axis of the eye of the device. This opening is closed off by an optic light filter so that only reduced daylight can enter. The viewing opening is also closed off by a transparent disk so that the entire device is hermetically closed off and is thus protected against the penetration of dust. This eliminates expensive servicing operations, as they are necessary in the state of the art. This is furthermore achieved by the adjustment of the visual signs and of the filters and also of the apertured diaphragms being carried out by a motor so that the housing does not need to have any further openings for handles, etc. All possible test variations are stored on the carrier for the visual signs so that these can be controlled, for example, by a stepping motor and keyboard or alternatively by a computer. This control has also at the same time the advantage that the complete data can be transmitted to a data processing system as a final result so that the work for the operator is minimized.

The device can also contain testing signs for the daytime visual acuity so that the device can be utilized as a combination device so that here both the daytime visual acuity and also the crepuscular visual acuity and the dazzle sensitivity can be tested.

BRIEF DESCRIPTION OF THE DRAWINGS

One exemplary embodiment of the invention will be described in greater detail hereinafter in connection with the drawings, in which.

DETAILED DESCRIPTION

Figure 1:
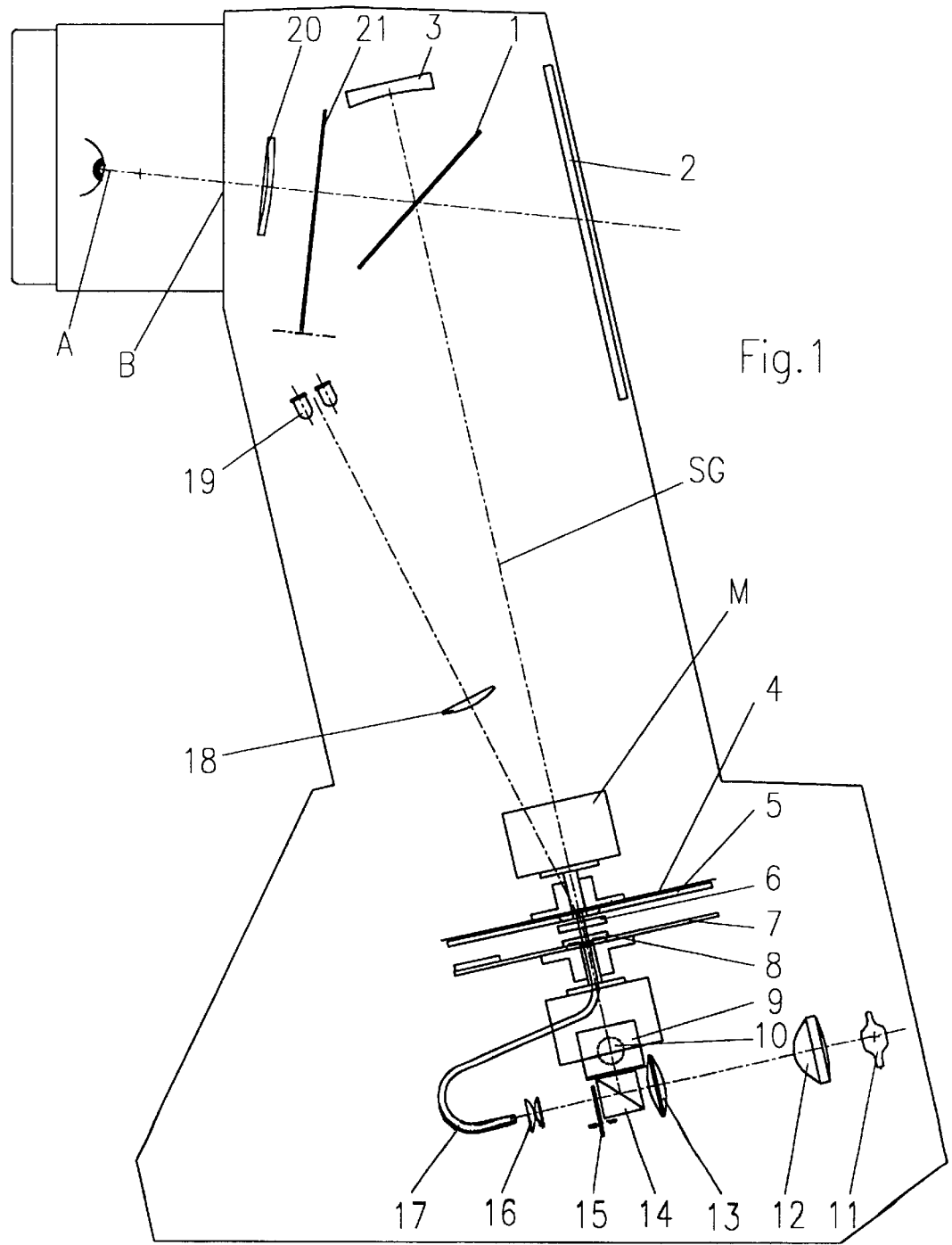
FIG. 1 is a cross-sectional side view of a device designed in accordance with the invention.
Figure 3:
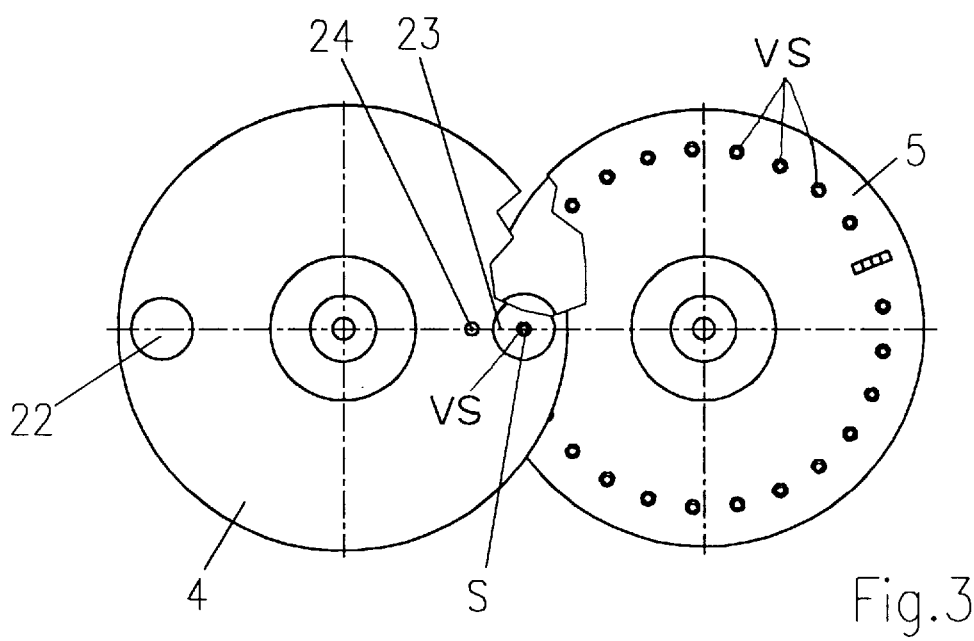
FIG. 3 is a cross-sectional view taken along the line III—III of FIG. 2.
Figure 4:
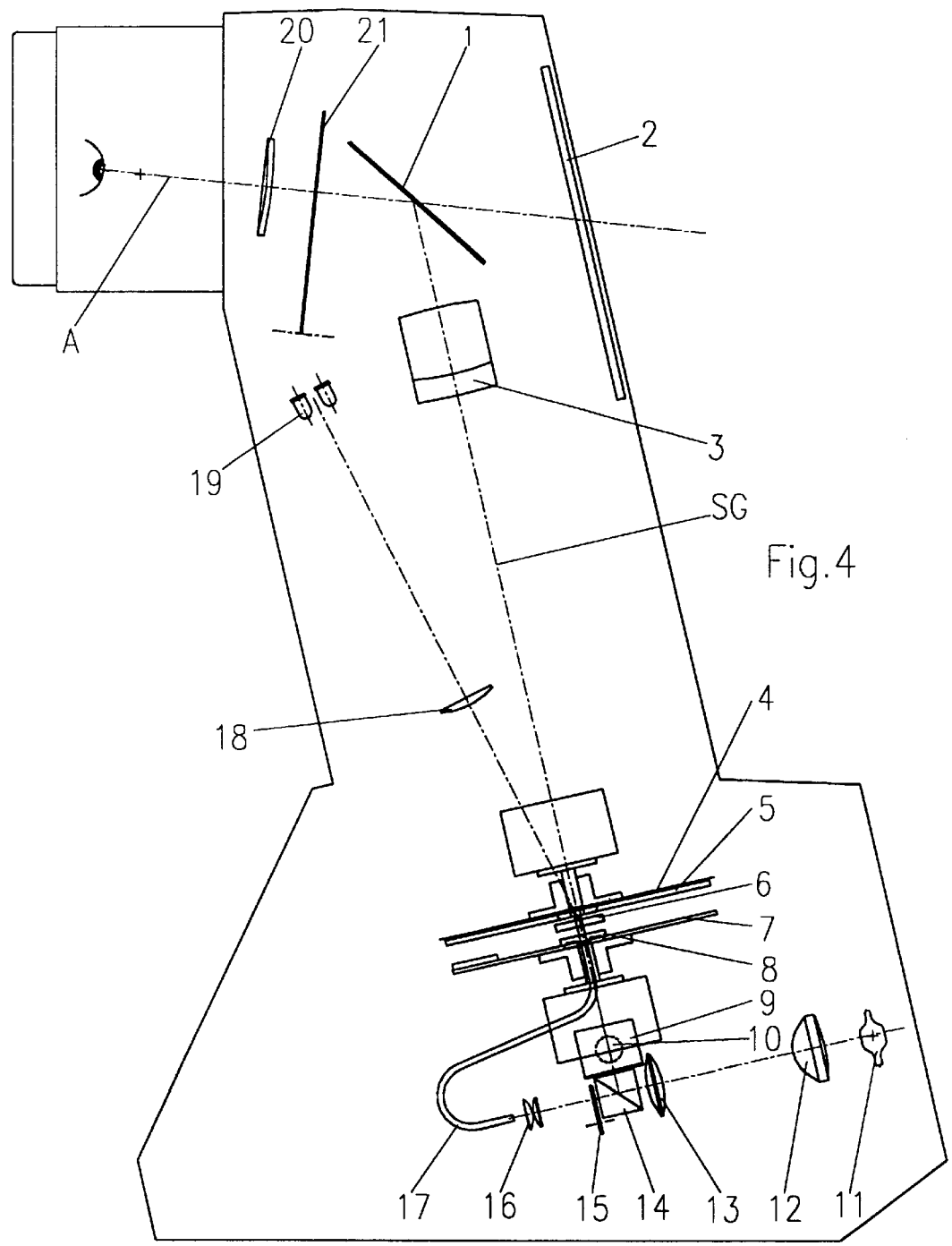
FIG. 4 is a further exemplary embodiment according to the invention.

FIG. 1 illustrates a cross-sectional side view of a vision-testing device of the invention, wherein the device has a viewing opening B for the eye. A partially transparent mirror 1 is arranged in an extension of the axis A of the eye. The device has furthermore an outlet opening in extension of the axis of the eye, into which opening an optic light filter 2 is inserted. The optic light filter 2 has the purpose of reducing the incoming daylight so that this device can be utilized in rooms with any type of lighting. A concentrating reflector 3 (or concave mirror) is inserted in FIG. 1 into the beam path SG extending to a visual sign located at S, and in the exemplary embodiment according to FIG. 4 an achromatic lens 3, wherein the visual sign location S is arranged at the focal point of the concentrating reflector or of the achromatic lens. The achromatic lens as well as the concentrating reflector extend over the entire width of the visual field. Aside from the fact that the exemplary embodiment according to FIG. 1 has a concentrating reflector and the exemplary embodiment according to FIG. 4 an achromatic lens, the exemplary embodiments have otherwise the same design. FIG. 3 refers thus to the exemplary embodiment according to FIG. 1, just as does FIG. 4.

The visual signs (optotypes) VS to be oriented at S are arranged on a visual sign carrier 5, which is designed as a disk. The visual sign carrier 5 is rotatably driven by a motor M. The motor M is a stepping motor which rotates the disk about its axis of rotation through pregiven angular positions so that the arcuately spaced visual signs VS will always be orientable at S in the beam path SG. Two openings 22 and 23 of the same size are provided on a second diaphragm disk 4 for the visual signs S. The difference between the two diaphragm openings is merely that next to the diaphragm opening 23 there is constructed a further diaphragm opening 24 whereat a terminal end of a fiber optic light conductor 17 is located to form the glare light source. Depending on the position of the diaphragm disk 4, either the light source 11 is blocked (or darkened) or is open so that the glare light source 17 is, respectively, not visible or the glare light source 17 is visible to the eye. The diaphragm disk 4 is also rotatably driven about its axis of rotation by a stepping motor.

A ground-glass disk 6 is arranged in the beam path SG and below the visual sign VS located at S, which disk 6 is used for the blending of the light exiting from the light source 11. A filter disk 7 is arranged coaxially to the vision-testing disk 5, which filter disk 7 carries a gray filter 8. This filter disk 7 is also rotatably driven about its axis of rotation by a stepping motor M, wherein same connects the gray filter 8 either into the beam path SG or removes same from said beam path. A different surrounding field is created on the testing field by said gray filter 8.

Figure 2:
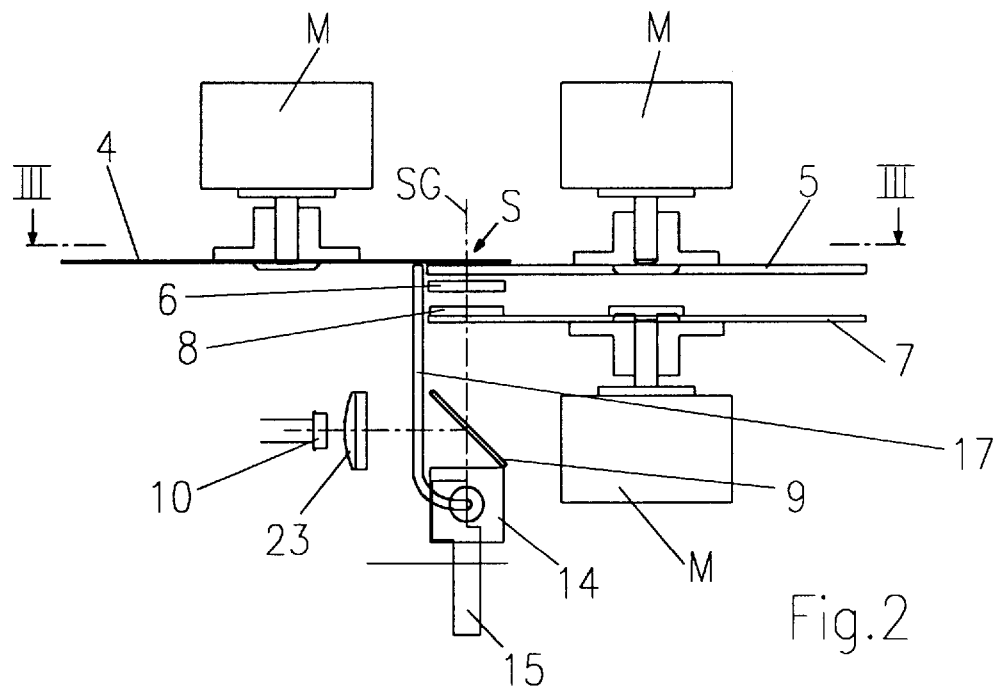
FIG. 2 is a side view of the lower part of the device according to FIG. 1, leaving out the contour of the housing.

The light source is a centered lamp 11 which projects light, when illuminated, through a condenser 12 and a further lens 13 and a splitting cube 14 to the testing field at S and the visual sign VS thereat. A certain portion of light is diverted by the splitting cube 14 and is fed through a condenser 16 to the fiber optic light conductor 17, the other end of which is used as a glare light source. A condenser 16 arranged in front of the input end of the fiber optic light conductor 17. Furthermore a diaphragm 15 lies in front of the condenser, which diaphragm can be swung more or less into and out of the light beam in order to adjust the brightness. FIG. 2 shows that between the splitting cube 14 and the visual sign VS at S there is arranged a partially transparent mirror 9. A portion of the light is diverted by this partially transparent mirror and is fed through a lens 23 to a photodiode 10. The photodiode detects the light intensity so that same can be regulated to its desired value.

Two light emitting diodes 19 are arranged above the vision-testing disk 5, which light diodes project light through a lens 18 oriented next to the visual sign location S. These light diodes are used to demonstrate (or indicate) the viewing direction since as a rule the testing field is very dark.

To examine the crepuscular myopy, it is possible to insert in addition into the beam path in front of the eyes two pairs of lenses 20 in order to determine whether the visual impression for the patient is improved by this addition. This test is preferably carried out without any dazzle. In addition, further diaphragms 21 can here be swung into and out of the beam path so that the test can also be carried out monocularly in order to preferably also test intraoculary lens patients.

All drives are controlled by motors and can be selected from one service area by pressing a key. The test can also be selectively performed in a specific sequence. As an alternative, a computer can also be directly used in place of a control device, wherein the computer then directly controls the motors M, wherein everything which the patient can recognize on the test is also visible for the examiner on the outside on the screen. This enables a direct better communication and the test results can be stored directly. Confusions due to an incorrect marking or entry of the result of dazzle when dazzle was not being tested are thus absolutely impossible.

The embodiments of the invention in which an exclusive property or privilege is claimed are defined as follows:

1. A vision-testing device, in particular for examining the crepuscular vision, with several visual signs which are to be randomly placed into the beam path, with a glare light source which can be selectively blocked and unblocked and is arranged next to a visual sign location, with a closed housing which has a viewing opening for the testing person and an opening lying in the extension of the axis of the eye, which opening indeed enables an unhindered looking out, however, is provided with a filter for restricting incoming outside light, wherein in extension of the axis of the eye there is arranged a partially transparent mirror inclined with respect to said axis, and a refractive element is arranged in the beam path extending from the eye to a selected visual sign oriented at the visual sign location, wherein the refractive element is one of an achromatic lens inserted into the beam path and covering the visual range of both eyes and a concentrating reflector having a focal point at the visual sign location, wherein a visual sign or visual signs to be oriented at are provided on a carrier and are transilluminated by a light source, wherein the carrier for the visual signs is arranged swingably or movably such that any visual signs provided on the carrier can be moved into the beam path, wherein a filter, in particular a gray filter, can be swung into the beam path between light source and visual sign location, wherein the glare light source is arranged stationarily next to the transilluminated visual sign location, and wherein above the visual sign carrier there are provided one or more diaphragms with varying diaphragm openings, which can be moved selectively into the beam path.

2. The vision-testing device according to claim 1, wherein the glare light source and the visual sign location are illuminated by the same light source.

3. The vision-testing device according to claim 2, wherein the glare light source includes a fiber optic light conductor coupled to the light source through a splitting mirror or a splitting cube.

4. The vision-testing device according to claim 2, wherein the light intensity of the glare light source can be adjusted by a diaphragm which can be moved into and out of the beam path to the fiber optic light conductor.

5. The vision-testing device according to claim 1, wherein the brightness of the light source is detected by a measuring device and can be regulated in dependency of a specified desired value.

6. The vision-testing device according to claim 1, wherein a ground-glass disk is inserted into the beam path and under the visual sign location.

7. The vision-testing device according to claim 1, wherein the carrier of the visual sign to be oriented at is a disk, onto the periphery of which the visual signs are applied.

8. The vision-testing device according to claim 7, wherein the disk consists of a transparent material.

9. The vision-testing device according to claim 7, wherein the diaphragm disk and the vision-testing carrier disk are arranged with parallel axes either coaxially or at a radial distance from one another.

10. The vision-testing device according to claim 9, wherein the filter is arranged on a further disk arranged at least coaxially with respect to the diaphragm disk or the visual sign carrier disk.

11. The vision-testing device according to claim 10, wherein all disks are driven by a motor (M).

12. The vision-testing device according to claim 11, wherein a control of the drives of the disks is computer controlled.

13. The vision-testing device according to claim 1, wherein the diaphragm is designed as a disk provided with openings.

14. The vision-testing device according to claim 1, wherein above the visual sign location there are provided one or several light sources, which through projection systems form fixation points next to the visual signs location.

15. The vision-testing device according to claim 14, wherein the light sources are light emitting diodes.

16. The vision-testing device according to claim 1, wherein one or several diaphragms for covering an eye can be moved into and out of the beam path between the eye and visual sign.

17. The vision-testing device according to claim 1, wherein meniscal lens pairs are arranged swingably into and out of the beam path in front of the eyes.

* * * * *